United States Patent [19]

Mihailovski

[11] 3,996,379
[45] Dec. 7, 1976

[54] MITICIDAL COMPOUNDS
[75] Inventor: Alexander Mihailovski, Berkeley, Calif.
[73] Assignee: Stauffer Chemical Company, Westport, Conn.
[22] Filed: Nov. 25, 1974
[21] Appl. No.: 526,862

Related U.S. Application Data

[63] Continuation of Ser. No. 217,702, Jan. 3, 1974, abandoned.
[52] U.S. Cl. .......................... 424/308; 260/471 R; 260/476 R; 424/309
[51] Int. Cl.² ...................... A01N 9/20; A01N 9/24
[58] Field of Search .................. 260/476 R, 471 R; 424/308, 309

[56] References Cited

UNITED STATES PATENTS 2,340,701  2/1944  Schlichting et al. ............... 260/456

OTHER PUBLICATIONS

Hatch et al., JACS, 72 p. 729 (1950).

Primary Examiner—Robert Gerstl
Attorney, Agent, or Firm—Michael J. Bradley

[57] ABSTRACT

Novel substituted benzoic acid and dibenzoic-acid-2-butyn-1-yl esters are disclosed. The compounds are useful as miticides.

1 Claim, No Drawings

MITICIDAL COMPOUNDS

This is a continuation, division of application Ser. No. 217,702 filed Jan. 3, 1974 now abandoned.

SUMMARY OF THE INVENTION

This invention relates to novel substituted aryl acid-2-butyn-1-yl esters and to their use as miticides. More particularly, this invention relates to compositions of matter having the formula:

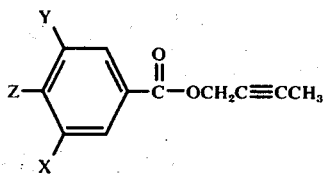

wherein X is selected from the group consisting of H, Br, Cl, and $NO_2$; Y is selected from the group consisting of H and $NO_2$; and Z is selected from the group consisting of H and Cl, with the provision that when Z is Cl, Y is H and X is Cl, and that X, Y, and Z are never simultaneously H, and the use of these compositions as miticides.

DETAILED DESCRIPTION OF THE INVENTION

In general, the compositions of the invention can be prepared by reacting a substituted benzoyl chloride with 2-butyn-1-ol in the presence of an acid acceptor. Thus, X, Y, and Z may be varied in the composition produced simply by the choice of an appropriately substituted benzoyl chloride. Where the acid acceptor is, e.g., a tertiary amine, the acceptor can also serve as a solvent for the reaction, although other solvents may be employed. The concentrations of the reactants employed are not critical and may be varied to some extent. Reactions of this type are normally exothermic so that the addition of heat is not required, and in fact, cooling is often necessary. The reaction will generally be carried out at a temperature of about 0° C to about 55° C, while the pressure employed is preferably atmospheric.

Preparation of the compositions of the invention is illustrated by the following examples:

EXAMPLE 1

2'butyn-1'-yl-3,4-dichlorobenzoate

A charge of 8.2 grams (0.043 mole) of 3,4-dichlorobenzoic acid and 11.9 grams (0.10 mole) of thionyl chloride is heated under reflux for about two hours. The reflux condenser is then removed and the excess thionyl chloride is evaporated by heating the reaction to about 140° C.

The residual liquid is cooled in an ice bath and a solution of 3.0 grams (0.043 mole) of 2-butyn-1-ol in 50 milliliters of pyridine is added slowly. The resulting mixture is stirred at room temperature for about 17 hours and then poured over crushed ice. The solid which forms is filtered and washed twice with 50 milliliter portions of 5 percent sodium bicarbonate and once with water. After drying, 9.5 grams of produce is obtained having a melting point of 69°–71° C. Yield is 91 percent of theory. Structure is confirmed by infrared and proton magnetic resonance spectroscopy.

EXAMPLE 2

2'butyn-1'-yl-3,5-dinitrobenzoate

The esterification procedure of Example 1 is followed, except that 3,5-dinitrobenzoyl chloride is employed instead of the 3,4-dichlorobenzoyl chloride. About 9.0 grams of product are obtained, having a melting point of 105.5°–108.5° C. Yield is 79 percent of theory. Structure is confirmed by infrared and proton magnetic resonance spectroscopy.

EXAMPLE 3

2'butyn-1'-yl-3-bromobenzoate

The esterification procedure of Example 1 is followed, except that 3-bromobenzoyl chloride is employed instead of the 3,4-dichlorobenzoyl chloride. About 17.6 grams of liquid product are obtained. Yield is 98 percent of theory. Structure is confirmed by infrared and proton magnetic resonance spectroscopy.

Compositions of matter which may be prepared according to the invention include:

(1) 2'-butyn-1'-yl-3,4-dichlorobenzoate
(2) 2'-butyn-1'-yl-3-bromobenzoate
(3) 2'-butyn-1'-yl-3-nitrobenzoate
(4) 2'-butyn-1'-yl-3-nitro-4-chlorobenzoate
(5) 2'-butyn-1'-yl-3,5-dinitrobenzoate
(6) 2'-butyn-1'-yl-3-bromo-4-chlorobenzoate
(7) 2'-butyn-1'-yl-3-bromo-5-nitrobenzoate In order to demonstrate the miticidal utility of the compositions, the following tests were conducted using the compounds designated above as 1, 2, 3 and 5.

Pinto bean plants (Phaseolus sp.) with expanded primary leaves were infested with 50 to 75 two-spotted mites [*Tetranychus urticae* (Koch)] of various ages. Aliquots of the toxicant, dissolved in an appropriate solvent, were diluted with water to which had been added 0.002 percent of a conventional wetting agent Sponto 221 (a polyoxy-ethylene sorbitanmonolaurate ether of alkylated phenol blended with organic sulfonates). Twenty-four hours after infestation, the plants are sprayed, to the point of runoff, with the aqueous suspensions of the toxicant. Test concentrations ranged from 0.05 percent to that at which 50 percent mortality is obtained. Mortality of adults and eggs is recorded after 48 hours and the LD-50 values are expressed as percent active ingredient in the aqueous suspensions. The results of the test are shown in the table.

TABLE

| Compound Numbers | Two-Spotted Mite | Two-Spotted Mite Eggs |
|---|---|---|
| (1) | 0.05 | >0.05 |
| (2) | 0.05 | >0.05 |
| (3) | 0.05 | >0.05 |
| (5) | 0.05 | >0.05 |

As may be seen from the test results, the compounds of the invention exhibit excellent miticidal activity. The compounds may be applied directly to the mites, or may be applied to a locus to be protected. In either event, it is, of course, necessary that the mites receive an effective or miticidal dosage or amount, i.e., an amount sufficient to kill the mites. Since the amount of active agent required will vary according to the mite treated and the conditions of application, precise limits on the amounts employed cannot be given. The tests set forth above indicate exemplary amounts which may be employed, as will readily be appreciated by those of skill in the art. Determination of the optimum effective concentration for a specific application is readily conducted by routine procedures, as will also be apparent to those skilled in the art.

The compounds are normally employed with a suitable carrier and may be applied as a dust, spray, drench, or aerosol. The compounds thus may be applied in combination with solvents, diluents, various surface active agents (for example, detergents, soaps or other emulsifying or wetting agents, surface active clays) carrier media, adhesives, spreading agents, humectants and the like. They may also be combined with other biologically active compositions, including fungicides, bactericides, insecticides, and algaecides, other miticides, etc., as well as with fertilizers, soil modifiers, etc. The compounds of the invention may be used in combination with an inert carrier and a surface active or emulsifying agent, and may also be applied in combination with other biologically active materials, in conjunction with a carrier and a surface active or emulsifying agent. The solid and liquid formulations can be prepared by any of the conventional methods well-known by those skilled in the art.

Various changes and modifications may be made without departing from the spirit and the scope of the invention described herein, as will be apparent to those skilled in the art to which it pertains.

What is claimed is:

1. A method of killing mites comprising applying to the mites or to a locus to be protected a miticidally effective amount of a compound having the formula:

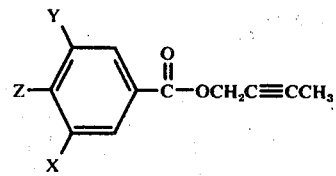

wherein X is selected from the group consisting of H, Br, Cl, and $NO_2$; Y is selected from the group consisting of H and $NO_2$; and Z is selected from the group consisting of H and Cl, with the provision that when Z is Cl, Y is H and X is Cl, and the X, Y, and Z are never simultaneously H.

* * * * *